(12) United States Patent
Spaans et al.

(10) Patent No.: US 6,784,273 B1
(45) Date of Patent: Aug. 31, 2004

(54) BIOMEDICAL POLYURETHANE, ITS PREPARATION AND USE

(75) Inventors: Coenraad Jan Spaans, Groningen (NL); Jacqueline Hermina de Groot, Leek (NL); Folkert Gerhardus Dekens, Groningen (NL); Albert Johan Pennings, Maaseik (BE)

(73) Assignee: Polyganics B.V., Groningen (NL)

( * ) Notice: Subject to any disclaimer, the term of this patent is extended or adjusted under 35 U.S.C. 154(b) by 0 days.

(21) Appl. No.: 09/701,622

(22) PCT Filed: Jun. 4, 1999

(86) PCT No.: PCT/NL99/00352
§ 371 (c)(1),
(2), (4) Date: Jun. 19, 2001

(87) PCT Pub. No.: WO99/64491
PCT Pub. Date: Dec. 16, 1999

(30) Foreign Application Priority Data

Jun. 5, 1998 (EP) ............................................. 98201868

(51) Int. Cl.$^7$ ............................................... C08G 18/10
(52) U.S. Cl. ........................ 528/65; 560/158; 521/173; 606/213
(58) Field of Search .......................... 528/65; 560/158; 521/173; 606/213

(56) References Cited

U.S. PATENT DOCUMENTS

| | | | | |
|---|---|---|---|---|
| 4,284,506 A | * | 8/1981 | Tetenbaum et al. | |
| 4,543,405 A | * | 9/1985 | Ambrose et al. | |
| 4,892,920 A | * | 1/1990 | Quay et al. | |
| 4,915,893 A | * | 4/1990 | Gogolewski et al. | |
| 5,100,992 A | * | 3/1992 | Cohn et al. | |

FOREIGN PATENT DOCUMENTS

| | | | |
|---|---|---|---|
| EP | 0295055 | * | 12/1988 |
| JP | 45020287 | * | 7/1970 |
| WO | 9922780 | * | 5/1999 |

OTHER PUBLICATIONS

De Groot et al., Use of Porous Polyurethanes for Meniscal Reconstruction..; Biomaterials; vol. 17, No. 2; Jan., 1996; pp. 163–173.*

De Groot et al.; "New Biomedical Polyurethane Urea With High Tear Strengths"; Polymer Bulletin; vol. 38, No. 2; Feb., 1997; pp. 211–218.*

* cited by examiner

*Primary Examiner*—Rachel Gorr
(74) *Attorney, Agent, or Firm*—Michaelson & Associates; Peter L. Michaelson; Arthur L. Liberman

(57) ABSTRACT

The invention is directed to a novel biomedical polyurethane based on diisocyanatae linked polyester polymer and diol components, said diol component having a uniform block-length.

24 Claims, 1 Drawing Sheet

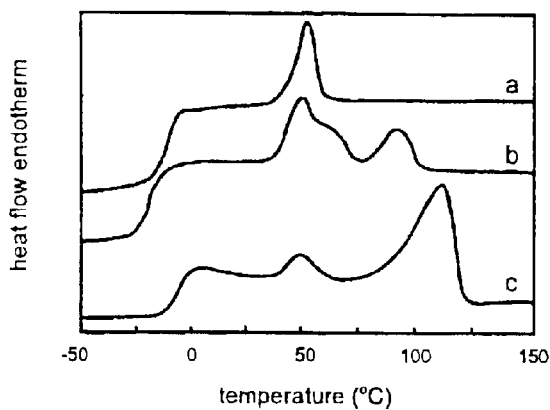

Figure 1. DSC thermogram of different ε-caprolactone and L-lactide based polyurethanes. a: Butanediisocyanate terminated copolymer prepolymer, chain extended with butanediol. b: Copolymer chain extended with butanediisocyanate end-capped butanediol block. c: 1,4-Butanediisocyanate terminated copolymer prepolymer, chain extended with butanediol end-capped 1,4-butanediisocyanate block.

BIOMEDICAL POLYURETHANE, ITS PREPARATION AND USE

The invention is directed to biomedical polyurethanes and the use thereof in various applications.

Biomedical polyurethanes (PUs) have been used for a wide range of applications. Examples include nerve guides, meniscal reconstruction materials, artificial skin and artificial veins.

For these applications, usually commercially available polyurethanes are used. These materials frequently exhibit good mechanical properties but an important disadvantage is that they contain aromatic diphenylmethane diisocyanate (MDI). MDI based polyurethanes are known to release carcinogenic and mutagenic products on degradation. Furthermore, they often show low resistance to tearing. A high resistance to tearing is important to prevent sutures from tearing out of a biomaterial. The development of new medical grade polyurethanes with good mechanical properties is therefore highly desirable.

Further an important aspect of the biomedical polyurethanes is the requirement that they can be processed into porous shaped bodies, e.g. as implants.

In the development of the novel materials of the invention, first porous 50/50 copoly($\epsilon$-caprolactone/L-lactide) materials were used for the reconstruction of meniscal lesions. They showed a very good adhesion to the meniscal tissue and, therefore, a good healing of the meniscal lesion. The mechanical properties of this copolymer resemble the mechanical properties of polyurethanes because of the high molecular weight and the presence of crystallisable L-lactide sequences. The polymer had, however, certain drawbacks. First, the degradation rate was somewhat too high New meniscal tissue, the so called fibrocartilage, is formed after an induct,on time of 10 to 20 weeks.

Second, due to the very high molecular weight of the polymer a maximum concentration of 5% could be reached. This resulted in very low compression moduli of porous materials. For the ingrowth of fibrocartilage higher moduli were needed. Finally, the L-lactide crystals, which are still present after 8 years of in-vitro degradation, may induce an inflammatory reaction since cells cannot digest them unlike poly($\epsilon$-caprolactone) and polyglycolide crystals.

To avoid lactide crystallinity, an amorphous 50/50 copoly($\epsilon$-caprolactone/85,15 L,D-lactide) was used for the production of nerve guides. Due to the absence of crystals, however, this polymer showed swelling upon degradation. Therefore, the focus was put on the synthesis of $\epsilon$-caprolactone and L-lactide based polyurethanes. The urethane hard segments crystals are likely to be small and susceptible to enzymatic degradation. In addition, by making an $\epsilon$-caprolactone and L-lactide based PU the biocompatibility may be improved.

When the copolymer was simply chain extended with diisocyanates, the mechanical properties of the resulting polymer were poor due to the absence of a phase separated morphology. Phase separated morphologies can be reached when an isocyanate terminated polyol is chain extended with a diamine or diol resulting in a polyurethane urea and polyurethane respectively. However, the L-lactide and $\epsilon$-caprolactone based prepolymer showed a deviant behavior with respect to chain extension using a diamine and diol. It appeared that the prepolymer was susceptible to aminolysis and transesterification unlike $\epsilon$-caprolactone and glycolide/trimethylene carbonate prepolymers.

The invention is directed to novel biomedical polyurethanes, suitable for implants, not having the disadvantages discussed above.

Further it is an aspect of the invention to provide a novel intermediate for this polyurethane, as well as a novel way of producing the polyurethane.

In a first aspect the invention is directed to novel biomedical polyurethanes, based on diisocyanate linked polyester (co)polymer and diol components, said diol component having a uniform block-length.

According to a preferred embodiment, the polyurethane may be represented by the following formula:

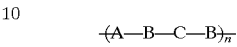

wherein the B denote diisocyanate moieties, A denotes a polyester moiety, C denotes a diol moiety and n is the number of recurring units.

In a most preferred embodiment the polyurethane consists of repeating units of the following formula

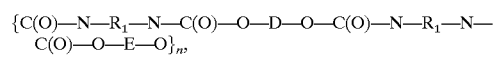

wherein $R_1$ is an n-butylene moiety, D is a polyester moiety, E is an n-butylene diol, an n-hexylene diol or a diethylene glycol based moiety and n indicates the number of repeating units.

With respect to the above formulae it is to be noted that they represent the recurring units of the polyurethane. The endgroups are not represented thereby. The nature of the endgroups will vary according to the type of (co)polyester and diol, as well as with the production process.

Further preferred embodiments of the invention are indicated in the dependent claims.

The products of the present invention show a good balance between the properties necessary for use thereof in biomedical applications, such as good modulus, tensile strength and compression modulus. It has been found possible to process these materials into porous implants by salt-leaching and freeze-drying, resulting in a material having macropores in the range of 150 $\mu$m to 300 $\mu$m. The material can also be produced in situ in an extruder, even in combination with generating macropores in situ.

As has been indicated above, the conventional methods of producing polyurethanes may result in transesterification and aminolysis, with the consequence that the material has insufficiently balanced properties. More in particular the uniformity of block-length gets lost, resulting in loss of phase separation. The consequence thereof is that the mechanical properties deteriorate to a level below that which is acceptable for numerous biomedical applications.

An important feature of these polyurethanes is that they owe their good mechanical properties to the phase separated morphology. Because the soft segments (e.g. polyesters, polycarbonates or polyethers) are chemically incompatible with the hard segments (urethane, urea or amide moieties) phase separation occurs. The hard segments crystallize and form strong hydrogen bonds with other hard segments resulting into physical cross-links.

The behavior of these polyurethanes is n strong contrast with other polyurethanes often applied. A well-known example is polyurethanes in which 2 different, chemically incompatible, soft segments (e.g. polyesters and polyethers) are coupled by a diisocyanate. An example thereof is disclosed in U.S. Pat. No. 4,2844,506. In this case, also a certain extent of phase separation will occur, but these materials do not owe their mechanical properties to the ability of the urethane functionality to form hydrogen bonds but to the contribution of entanglements and phase separation between the different soft segments. The reason why the urethane functionalities can not contribute to the mechanical properties of the material is that the urethane moieties are too small to crystallize and form hydrogen bonds.

Polyurethanes with a micro-phase separated morphology frequently exhibit good mechanical properties and are generally easy to process due to the relatively low melting point.

Mechanical properties of polyurethane ureas are usually even better resulting from the increased crystallizability and hydrogen bonding ability of the urea moieties. The polymers, however, frequently have melting points that are close to the degradation temperature, leading to a small processing window.

The polymers of the present invention, contain long urethane-based hard segments of uniform size. This results into a system wherein the hard segments have increased crystallizability and hydrogen bonding ability compared to "classical" polyurethanes. The mechanical properties are comparable to those of polyurethane ureas. However, the melting point is still rather low which makes processing relatively easy.

It should be noted that the uniformity of the urethane-based hard segments is the crucial factor for the mechanical properties of the materials. The preferred method for the synthesis of these polyurethanes should therefore be the reaction of the diol component with an excess of diisocyanate followed by reaction with the macro-diol (e.g. poly-caprolactone or copolymers of L-lactide and caprolactone). In this process, trans-esterification of the soft segment with the chain extender is avoided, resulting into hard segments of uniform size.

As has been indicated above, the polyurethane of the invention comprises in the most general form diisocyante linked diol and polyester, more in particular linear random copolyester, components. The nature of the diol component is very important, especially with respect to the uniformity of the block-length. The diol and the (linear random co)polyester are connected to each other by diisocyanate, more in particular 1,4-butane diisocyanate.

The polyurethane of the present invention car be prepared by different processes. In a first process the diol component, i.e. the butanediol, hexaneddiol or diethylene glycol, or the reaction product of two molecules of the said diol with 1,4-butanediisocyanate (BDO-BDI-BDO), is reacted with an isocyanate terminated polyester, i.e. the reaction product of the random polyester with an excess of BDI (BDI-polyester-BDI). By selection of the reaction conditions (temperature, time, catalyst, and the like) the molecular weight of the polyurethane may be selected.

In the alternative the diol component is end-capped with the BDI and reacted with the random copolyester.

According to a further method it is possible to end-cap the polyester with the isocyanate endcapped diol component resulting (in the case of a dihydroxy terminated polyester) in a prepolymer of the following composition:

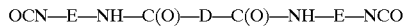
OCN—E—NH—C(O)—D—C(O)—NH—E—NCO

This prepolymer can subsequently be reacted with water to yield a polyurethane urea according to the invention. This process provides the possibility to generate porous materials in situ, for example by mixing the prepolymer with salt and water, and letting the material react for some time at a suitable temperature. After leaching the salt from the material a porous polyurethane urea has been obtained, whereby part of the pores are provided by the salt and part by the $CO_2$ generated in the reaction of the prepolymer with the water.

The reactions between the various components are carried out under the conditions known to be suitable for the preparation of polyurethanes.

These processes all result in a useful biomedical polyurethane, having the advantageous properties cited above. It is to be noted that the use of an isocyanate endcapped diol has preference, especially in case the polyester component has the tendency to transesterify.

After the preparation of the base material it is possible to process it further, e.g. from a solution in an organic solvent such as dioxane, into shaped materials. For some applications it is useful to have a porous structure. This can be obtained by the method as described in De Groot et al, Use of biodegradable polymer implants in meniscus reconstruction, Colloid Polym. Sci., 1990, 268, 1073–1081. In case of the use of the polyurethane of the invention in meniscus reconstruction, it is useful to have porosities of 50 to 99 vol. %.

The diol component to be used in the present invention has to meet the requirement of uniform block-length. In practice this will mean that at least 90%, preferably at least 98% of the diol component molecules will have the same block-length. Suitable diol components can be based on 1,4-butanediol, 1,6-hexanediol or diethylene glycol. It is possible to use the diol as such, but it is also possible to use a reaction product of a diisocyanate (e.g. 1,4-butanediisocyanate) and two molecules of the diol (BDO-BDI-BDO). Optionally one may end-cap this reaction product with two molecules of BDI, resulting in a five-block, that can be used in the reaction with the linear random copolyester.

The polyester to be used in accordance with the invention will preferably be linear, more in particular be a random copolyester, and will have reactive endgroups. These endgroups may be hydroxyl or carboxyl. It is preferred to have a dihydroxy terminated copolyester, but hydroxy-carboxyl or dicarboxyl terminated copolyesters can also be used. The nature of the endgroups is determined by the type of comonomers, the amounts thereof, the type of starter (if used), and the reaction conditions. It is to be noted, that the molecular weight of the polyurethane in the present invention is not so crucial for obtaining the necessary mechanical properties, as is the case in the prior art. Accordingly, lower molecular weights often suffice.

Suitable monomers for the polyester are the cyclic monomers that can be polymerised under ring-opening polymerisation conditions. Examples are lactides, glycolides, trimethylene carbonate and/or ε-caprolacton. Preferred are lactide (D, L, D-L, meso) and ε-caprolacton. More in particular a linear random copolyester having about equimolar amounts of ε-caprolacton and L-Lactide is preferred. Other possibilities include polyesters based on succinic acid and ethylene glycol or 1,4-butanediol, or on (co)polyesters of lactic acid. In case the polyester has to be linear, it can be prepared using a difunctional component (diol) as starter, but in case a three or higher functional polyol is used, star shaped polyesters may be obtained.

The conditions for preparing the polyesters are those known in the art.

The invention is now elucidated on the basis of the examples.

Experimental

Materials

L-lactide and ε-caprolactone were obtained from Hycail bv. (Noordhorn, The Netherlands) and used after standard purification. The catalyst stannous octoate ($SnOct_2$) was obtained from Sigma Corp. USA and used directly from the supplier. 1,4-Butane diisocyanate (DSM, Geleen, The Netherlands) was distilled under reduced nitrogen pressure; 1,4-butanediol (BDO, Acros Organics) from 4 Å molecular sieves, dimethyl sulfoxide (DMSO, Acros Organics) from $CaH_2$.

Prepolymer Synthesis

For the 50/50 L-lactide and ε-caprolactone, 20 gram of L-lactide (0.14 mol) was mixed with 16 gram ε-caprolactone (0.14 mol) under nitrogen atmosphere. 1.70 gram butanediol (18.87 mmol) and 40 mg stannous octoate were added as initiator and catalyst respectively. The mixture was polymerized for 24 hours at 130° C. $^1$H-NMR showed complete conversion.

Block Synthesis

The isocyanate terminated urethane block (BDI/BDO/BDI) was prepared by reaction of butanediol with a six-fold excess of butanediisocyanate at 80° C. without catalyst for 5 hours. The excess disocyanate was removed by washing with dry hexane.

The hydroxyl terminated urethane block (BDO/BDI/BDO) was prepared by mixing butanediisocyanate with a six-fold excess of butanediol at 80° C. without catalyst, for five hours. The excess butanediol was removed by washing with dry acetone.

Polymerization

The prepolymer (50/50 ε-caprolactone/L-lactide) or the diisocyanate end-capped prepolymer was dissolved in DMSO. The chain extender butanediol or block were dissolved in DMSO. The chain extender solution was added drop wise to the prepolymer solution under mechanical stirring. The total polymer concentration after chain extension was 5 w/w % in the case of butanediamine, 30 w/w % in the case of the isocyanate terminated block and 50 w/w % for butanediol and the hydroxyl terminated block.

Characterization

Intrinsic viscosities were measured using a Ubbelohde viscometer.

Calorimeter studies were carried out with a Perkin Elmer DSC 7 calorimeter. The scanning rate was 10° C. per minute.

$^1$H-NMR (200 MHz) was used to characterize the blocks.

Tear strength and hysteresis were determined.

TABLE 1

| | Prepolymer | chain-extender |
|---|---|---|
| a | Isocyanate terminated prepolymer* | BDO |
| b | Prepolymer* | BDI/BDO/BDI |
| c | Isocyanate terminated prepolymer* | BDO/BDI/BDO |

*50/50 L-lactide/ε-caprolactone 2000

When the butanediisocyanate terminated prepolymer was chain extended with a BDI-BDO-BDI block (table 1, b), a polymer with an intrinsic viscosity of 1.0 dl/g could be made. The DSC thermogram of the polymer is shown in FIG. 1. The mechanical properties of the products based on a–c (table 1) are presented in table 2.

TABLE 2

| (η) (dl/g) | Modulus (MPa) | Tensile Strength (MPa) | Strain at break (%) | Tm (° C.) | ΔH (J/g) | Tg (° C.) | Permanent Deformation (%) |
|---|---|---|---|---|---|---|---|
| 1.8 | 12 | 12 | 750 | 53 | 5.5 | −9 | 13.5 |
| 1.0 | 60 | 23 | 640 | 50, 92 | 8.6, 4.6 | −21 | 13.5 |
| 2.0 | 62 | 44 | 560 | 49, 112 | 2.3, 16 | −5 | 10.0 |

These experiments show that the method b of table 1 provides products with better mechanical properties, than method a.

The role of the uniformity of the hard segments has also been demonstrated by the following example:

Polycaprolactone (M=2000) was end-capped with an excess of 1,4-butanediisocyanate. The excess of diisocyanate was removed by distillation. The resulting macrodiisocyanate was chain-extended with the BDO.BDI.BDO block. The resulting polyurethane had an intrinsic viscosity of 2.00 dL/g and a modulus of 70 MPa.

When polycaprolactone (M=2000) was chain-extended with a BDI.BDO.BDI.BDO.BDI block, a polyurethane of identical composition was obtained. However, in this case trans-esterification reactions of the chain-extender with the polycaprolactone soft segment were avoided. This resulted into a polymer with an intrinsic viscosity of 1.00 dL/g and a modulus of 105 MPa. The lower viscosity of the polymer can be explained by the lower reactivity of the BDI.BDO.BDI.BDO.BDI block compared to the BDO.BDI.BDO block. However, the modulus has significantly increased. This is a result of the uniform hard segments. Hard segments of uniform size are more crystalline and thus more difficult to disrupt.

The absence of a melting endotherm at 60 ° C. provides additional evidence that by this method trans esterification reactions were avoided.

BRIEF DESCRIPTION OF THE DRAWING

FIG. 1 is a DSC thermogram of three different ε-caprolactone and L-lactide based polyurethanes.

DETAILED DESCRIPTION OF THE DRAWING

Referring to FIG. 1, the DSC thermogram of three different ε-caprolactone and L-lactide based polyurethanes, the term 'copolymer' is intended herein to mean: "50:50 copolymer of ε-caprolactone and L-lactide". The graph indicated by reference letter a is for a butanediisocyanate-terminated copolymer prepolymer, chain extended with butanediol. The graph indicated by reference letter b is for the 50:50 ε-caprolactone—L-lactide copolymer chain-extended with butanediisocyanate end-capped butanediol block, The graph indicated by reference letter c is for the 1,4 butane diisocyanate-terminated copolymer prepolymer, chain extended with butanediol end-capped with 1,4 butane diisocyanate block.

What is claimed is:

1. A biomedical biocompatible polyurethane based on (i) a diisocyanate linked polyester polymer component and (ii) a diol component, said polyurethane having the formula ─(A—B—C—B─)$_n$ wherein A denotes said polyester component, B denotes said diisocyanate moiety, C denotes said diol component, n denotes the number of recurring units, and wherein at least 90% of the diol components, C, have the same block length, wherein the polyester component is a random copolyester component and is a copolyester component having at least two of a moiety selected from the group consisting of lactide, glycolide, trimethylene carbonate and ε-caprolactone.

2. A biomedical biocompatible polyurethane produced according to a process comprising the steps of (i) reacting the polyester with an isocyanate end-capped diol component in order to form a prepolymer, the ratio of isocyanate end-groups to polyester end-groups being at least 2:1, and then (ii) reacting the resulting prepolymer with water.

3. A biomedical biocompatible polyurethane according to claim 2, based on a copolyester of lactide and ε-caprolactone containing 5 to 95% of units of lactide and 5 to 95% of units of ε-caprolactone, based on the total number of monomeric units in the polymer.

4. A biomedical biocompatible polyurethane based on (i) a diisocyanate linked polyester polymer component and (ii) a diol component, said polyurethane having the formula ─(A—B—C—B)ₙ wherein A denotes said polyester component, B denotes said diisocyanate moiety, C denotes said diol component, n denotes the number of recurring units, and wherein at least 90% of the diol components, C, have the same block length, comprising from 40 up to 60% of units of lactide, based on the total number of monomeric units in the polymer.

5. A biomedical biocompatible polyurethane based on (i) a diisocyanate linked polyester polymer component and (ii) a diol component, said polyurethane having the formula ─(A—B—C—B)ₙ wherein A denotes said polyester component, B denotes said diisocyanate moiety, C denotes said diol component, n denotes the number of recurring units, and wherein at least 90% of the diol components, C, have the same block length, comprising from 40 up to 60% of units of ε-caprolactone, based on the total number of monomeric units in the polymer.

6. A process for the preparation of a biomedical biocompatible polyurethane based on (i) a diisocyanate linked polyester polymer component and (ii) a diol component, said polyurethane having the formula ─(A—B—C—B)ₙ wherein A denotes said polyester component, B denotes said diisocyanate moiety, C denotes said diol component, n denotes the number of recurring units, and wherein at least 90% of the diol components, C, have the same block length, comprising the steps of (i) reacting at least two moles of a diisocyanate with one mole of a diol selected from the group consisting of 1,4-butanediol, 1,6-hexanediol, diethyleneglycol and the reaction product of two molecules of said diol with the diisocyanate to form a first reaction product and (ii) reacting a polyester with said first reaction product.

7. A biomedical biocompatible polyurethane based on (i) a diisocyanate linked polyester polymer component and (ii) a diol component, said polyurethane having the formula ─(A—B—C—B)ₙ wherein A denotes said polyester component, B denotes a 1,4-butane diisocyanate moiety, C denotes said diol component, n denotes the number of recurring units, wherein at least 90% of the diol components, C, have the same block length and wherein the polyester component is based on (i) at least one carboxylic acid selected from the group consisting of lactic acid and succinic acid and (ii) at least one diol selected from the group consisting of ethylene glycol, 1,4-butanediol, 1,6-hexanediol and diethylene glycol.

8. A process for the preparation of a biomedical biocompatible polyurethane based on (i) a diisocyanate linked polyester polymer component and (ii) a diol component, said polyurethane having the formula ─(A—B—C—B)ₙ wherein A denotes said polyester component, B denotes a 1,4-butane diisocyanate moiety, C denotes said diol component, n denotes the number of recurring units, and wherein at least 90% of the diol components, C, have the same block length, comprising the steps of (i) reacting at least 2 moles of 1,4-butane diisocyanate with 1 mole of a polyester to form a first reaction product and (ii) reacting a diol selected from the group consisting of 1,4-butanediol, 1,6-hexanediol, diethylene-glycol and the reaction product of two molecules of said diol with the 1,4-butane diisocyanate with said first reaction product.

9. A method for reconstruction of at least one meniscal lesion comprising the step of effecting an adhesive implant to meniscal tissue having at least one of said lesions of a meniscus-reconstructing quantity at a meniscus-reconstructing rate of at least one polyurethane based on (i) a diisocyanate linked polyester polymer component and (ii) a diol component, said polyurethane having the formula ─(A—B—C—B)ₙ wherein A denotes said polyester component, B denotes a 1,4-butane diisocyanate moiety, C denotes said diol component, n denotes the number of recurring units, and wherein at least 90% of the diol components, C, have the same block length, for a fibrocartilage induction time of from 10 up to 30 weeks.

10. A process for preparing a biomedical biocompatible polyurethane based on (i) a diisocyanate linked polyester polymer component and (ii) a diol component, said polyurethane having the formula ─(A—B—C—B)ₙ wherein A denotes said polyester component, B denotes said diisocyanate moiety, C denotes said diol component, n denotes the number of recurring units, and wherein at least 90% of the diol components, C, have the same block length comprising the steps of:

i. admixing equimolar quantities of L-lactide and ε-caprolactone in the presence of a stannous octoate catalyst and a butanediol initiator thereby forming a L-lactide-ε-caprolactone prepolymer;

ii. admixing butanediol with a six-fold excess of butane diisocyanate thereby forming an isocyanate-terminated urethane block;

iii. dissolving the L-lactide-ε-caprolactone prepolymer in dimethyl sulfoxide to form a first solution;

iv. dissolving the isocyanate-terminated block in dimethyl sulfoxide to form a second solution;

v. admixing the first solution with the second solution to form a polyurethane reaction mass;

vi. recovering the resulting urethane ploymer from the reaction mass.

11. A biomedical biocompatible polyurethane based on (i) a diisocyanate linked polyester polymer component and (ii) a diol component, said polyurethane having the formula ─(A—B—C—B)ₙ wherein A denotes said polyester component, B denotes said diisocyanate moiety, C denotes said diol component, n denotes the number of recurring units, and wherein at least 90% of the diol components, C, have the same block length wherein the polyester component is based on a linear random copolyester.

12. A polyurethane according to claim 11 wherein B is a 1,4-butane diisocyanate component.

13. A polyurethane according to claim 11 where C is selected from the group consisting of butanediol components, hexanediol components, diethylene glycol components and reaction products of the diisocyanate moiety and two molecules of the diol component.

14. A biomedical biocompatible polyurethane according to claim 11 consisting of repeating units of the following formula:

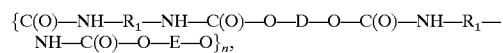

wherein R₁ is an n-butylene moiety, D is a polyester moiety, E is an n-butylene diol, an n-hexylene diol or a diethylene glycol based moiety and n indicates the number of repeating units.

15. A biomedical biocompatible polyurethane according to claim 11 consisting of repeating units of the following formula:

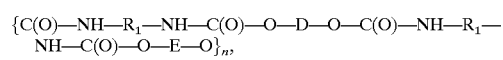

wherein R₁ is an n-butylene moiety, D is a polyester moiety, E is selected from the group consisting of n-butylene, n-hexylene, —CH₂—CH₂—O—CH₂—CH₂— and —XYX—, wherein X is selected from the group consisting of an an n-butylene glycol-based moiety, an n-hexylene glycol-based moiety and a diethylene glycol-based moiety and Y is a 1,4-butane diisocyanate-based moiety resulting from the reaction of 1,4-butane diisocyanate with a diol selected from the group consisting of n-butylene glycol, n-hexylene glycol and diethylene glycol, with the mole ratio of glycol:diisocyanate being 2:1.

16. A biomedical biocompatible polyurethane according to claim 11, wherein the polyester component is based on a polyester prepared by ring opening polymerization.

17. A biomedical biocompatible polyurethane according to claim 11, wherein the polyester component is based on (i) at least one carboxylic acid selected from the group consisting of lactic acid and succinic acid and (ii) at least one diol selected from the group consisting of ethylene glycol, 1,4-butanediol, 1,6-hexanediol and diethylene glycol.

18. A process for the preparation of a biomedical biocompatible polyurethane defined according to claim 11 comprising the steps of (i) reacting at least 2 moles of a diisocyanate with 1 mole of a polyester to form a first reaction product and (ii) reacting a diol selected from the group consisting of 1,4-butanediol, 1,6-hexanediol, diethylene-glycol and the reaction product of two molecules of said diol with the diisocyanate with said first reaction product.

19. An implant constructed from at least one biomedical biocompatible polyurethane defined according to claim 11 having a porosity of 50 to 99 vol. %.

20. A method for reconstruction of at least one meniscal lesion comprising the step of effecting an adhesive implant to meniscal tissue having at least one of said lesions of a meniscus-reconstructing quantity at a meniscus-reconstructing rate of at least one polyurethane defined according to claim 11 for a fibrocartilage induction time of from 10 up to 30 weeks.

21. A biomedical biocompatible polyurethane based on (i) a diisocyanate linked polyester polymer component and (ii) a diol component, said polyurethane having the formula $(A-B-C-B)_n$ wherein A denotes said polyester component, B denotes said diisocyanate moiety, C denotes said diol component, n denotes the number of recurring units, and wherein at least 90% of the diol components, C, have the same block length, wherein the polyester component is based on a linear random copolyester, said biocompatible polyurethane having a phase separated morphology, comprising (i) soft segments consisting of polyester components and (ii) urethane-based hard segments of uniform size, said hard segments consisting of diol components having a uniform block-length, and wherein the diol components and the polyester components have been linked to a diisocyanate component by means of reaction thereof with a diisocyanate.

22. A biomedical biocompatible polyurethane according to claim 11, wherein the block-length is the same for at least 98% of the diol units.

23. A biomedical biocompatible polyurethane according to claim 11, wherein the diisocyanate is an aliphatic diisocyanate.

24. A biomedical biocompatible polyurethane according to claim 11 wherein the diisocyanate-linked polyester component is a 1,4-butane diisocyanate-linked polyester component.

* * * * *